(12) United States Patent
Jones et al.

(10) Patent No.: US 6,746,449 B2
(45) Date of Patent: *Jun. 8, 2004

(54) SPINAL ROD TRANSLATION INSTRUMENT

(75) Inventors: Robert J. Jones, Austin, TX (US); Eric Loveless, Jacksonville, FL (US); William A. Cottle, Vancouver (CA)

(73) Assignee: Spinal Concepts, Inc., Austin, TX (US)

( * ) Notice: Subject to any disclaimer, the term of this patent is extended or adjusted under 35 U.S.C. 154(b) by 142 days.

This patent is subject to a terminal disclaimer.

(21) Appl. No.: 09/952,209

(22) Filed: Sep. 12, 2001

(65) Prior Publication Data

US 2002/0095153 A1 Jul. 18, 2002

(51) Int. Cl.$^7$ .............................................. A61B 17/56
(52) U.S. Cl. ........................................................ 606/61
(58) Field of Search ............................ 606/61, 86, 90, 606/101, 104, 105, 205–208

(56) References Cited

U.S. PATENT DOCUMENTS

| | | |
|---|---|---|
| 4,505,268 A | 3/1985 | Sgandurra |
| 4,611,581 A | 9/1986 | Steffee |
| 4,763,644 A | 8/1988 | Webb |
| 4,805,602 A | 2/1989 | Puno et al. |
| 4,887,596 A | 12/1989 | Sherman |
| 4,950,267 A | 8/1990 | Ishihara et al. |
| 5,020,519 A | 6/1991 | Hayes et al. |
| 5,129,388 A | 7/1992 | Vignaud et al. |
| 5,219,349 A | 6/1993 | Krag et al. |
| 5,364,397 A * | 11/1994 | Hayes et al. ................... 606/61 |
| 5,545,166 A | 8/1996 | Howland |
| 5,571,102 A | 11/1996 | Cavagna et al. |
| 5,630,816 A | 5/1997 | Kambin |
| 5,649,926 A | 7/1997 | Howland |
| 5,782,831 A | 7/1998 | Sherman et al. |
| 5,910,141 A * | 6/1999 | Morrison et al. ............. 606/61 |
| 5,961,518 A | 10/1999 | Errico et al. |
| 5,977,539 A | 11/1999 | Holzapfel et al. |
| 5,989,250 A | 11/1999 | Wagner et al. |
| 6,063,089 A | 5/2000 | Errico et al. |
| 6,132,430 A | 10/2000 | Wagner |
| 6,440,133 B1 * | 8/2002 | Beale et al. ................... 606/61 |

* cited by examiner

Primary Examiner—Kevin Shaver
Assistant Examiner—Michael B. Priddy
(74) Attorney, Agent, or Firm—Beth A. Vrioni (57) ABSTRACT

An instrument may be used to move a rod attached to vertebrae to an opening of a fixation device. Positioning the rod in the opening may properly align the vertebrae with respect to the vertebra attached to the fixation element. A fixation holder may be coupled to the fixation element. The holder may include a protrusion. The protrusion may engage a guide of the instrument during use. The protrusion and the guide may ensure that the rod is properly positioned within the opening in the connector. The instrument and holder may automatically align the rod to the opening without requiring manual manipulation of the rod or the fixation element. The fixation element may include a connector. The connector may be positioned within the fixation element so that removal of the connector from the fixation element is inhibited.

52 Claims, 8 Drawing Sheets

SPINAL ROD TRANSLATION INSTRUMENT

BACKGROUND OF THE INVENTION

1. Field of the Invention

The present invention generally relates to spinal fixation systems for correction of spinal deformities or injuries, and embodiments of the invention relate to an instrument for moving a vertebra or vertebrae to a desired position.

2. Description of Related Art

Spinal disorders, degenerative conditions, or trauma may result in a need to correct or stabilize the spine of a patient. A variety of spinal fixation systems may be used to correct and/or stabilize a spine. A spinal fixation system may be classified as an anterior, lateral, or posterior system according to a position of the system relative to the spine. Anterior and lateral spinal fixation systems usually include short structures that support only a few adjacent vertebral bodies of a spine. Several anterior and lateral spinal fixation systems may be coupled to vertebral bodies to correct and/or stabilize a large portion of the spine. Posterior stabilization systems often include pairs of vertically aligned rods for stabilizing both short and long segments of a spine.

A posterior spinal fixation system may include a pair of bendable rods that are contoured and longitudinally disposed adjacent to vertebral bodies of a spine. Rods used in a fixation system are typically circular in cross section, although rods having non-circular cross sections may also be used. The rods may be attached to vertebral bodies of the spine by a plurality of fixation elements. The fixation elements may be hooks and/or bone screws. Transverse connectors may be used to join the pair of spinal rods together. Transverse connectors may stabilize and provide rigidity to a spinal fixation system.

A fixation element may include a connector that attaches the fixation element to a spinal rod. One type of connector includes an opening that snaps onto a spinal rod. When a spinal rod is positioned in the opening of a connector, a fastener, such as a bolt or a locking plate, may securely attach the connector to the fixation element. The fastener may inhibit motion of the spinal rod relative to the fixation element. U.S. Pat. No. 6,132,430 issued to Wagner, which is incorporated by reference as if fully set forth herein, describes fixation elements wherein fixation element connectors are configured to snap onto spinal rods. Other types of fixation elements may also be used in a spinal fixation system. Fixation elements may include, but are not limited to, the fixation elements shown and described in U.S. Pat. Nos. 4,763,644; 4,805,602; 4,887,596; 4,950,269; 5,129,388; 5,961,518; 5,989,250; 5,997,539; and 6,063,089; each of these patents being incorporated by reference as if fully set forth herein.

A spinal rod may be attached to one or more vertebrae during a posterior spinal fixation procedure. A vertebra or vertebrae that are not in desired positions may be moved during a spinal fixation procedure. A fixation element may be attached to a vertebra that needs to be moved. A translation instrument may be used to draw the fixation element and the spinal rod together. A fastener may then be attached to the fixation element to join the rod and the element together.

A translation device that may be used to join a fixation element and a spinal rod together is the Universal Spinal System Rod Introduction Pliers from Synthes Spine (Paoli, Pa.). One of the jaws of the pliers has a hollow barrel. The other jaw is a rod contactor. The pliers are used with a holder that threadably attaches to a fixation element. After attaching the holder to the fixation element, the holder is inserted into the hollow barrel. Grips of the pliers are squeezed together by a user to cause the rod contactor to rotate and contact a spinal rod. Continued squeezing of the grips forces the rod and the fixation element together so that the rod may be positioned within an opening of the fixation element. A user of the translation device must adjust the position of the holder within the barrel to ensure that the rod is positioned within the fixation element when the grips of the translation device are closed together. Proper alignment of the translation device may be difficult to achieve during use of the translation instrument. A user may have to manually adjust the vertical position of the fixation element while simultaneously translating the fixation element and the rod together.

U.S. Pat. No. 5,020,519 to Hayes et al., which is incorporated by reference as if fully set forth herein, describes a device that may be used to introduce a rod into an opening in a spinal implant. The system includes a one-piece tool that clamps a spinal implant and aligns a rod with an opening in the spinal implant. The device may be used to reduce the vertical offset between the rod and the implant. The spinal implant must be maintained in the correct position in the translation device while threading the rod into place between the jaws.

SUMMARY OF THE INVENTION

A translation instrument may be used to move a vertebra or vertebrae to a desired position. A spinal rod may be attached to vertebral bodies by fixation elements. An adjacent fixation element may be attached to an out-of-position vertebra. It may be desirable to move the spinal rod and the adjacent fixation element together so that the vertebra is placed in a desired position relative to adjacent vertebrae. Securing the fixation element to the spinal rod may allow for proper alignment of vertebral bodies of a spinal column.

A translation instrument may be used to move the spinal rod and the adjacent fixation element together. The translation instrument may simultaneously translate the fixation element towards the rod and adjust the vertical height of the fixation element relative to the rod so that the rod is positioned within a rod opening of the fixation element. A guide of the translation instrument may engage the fixation element or an extension member coupled to the fixation element. The guide may ensure that the spinal rod is properly positioned relative to a fixation element when the translation instrument is used.

A fixation element may be coupled to a vertebral body whose position is to be adjusted. A fixation element may be, but is not limited to, a bone screw or a hook. A holder may be coupled to the fixation element. The holder may include an attachment mechanism, a shaft, and a guide. The attachment mechanism may securely attach the holder to the fixation element. The shaft may allow the holder to be coupled to a positioner of a translation instrument. The holder guide may be a protrusion that extends from a side of the shaft.

A translation instrument may include a positioner, an arm, and an actuator. A positioner may couple a fixation element holder to the translation instrument. In an embodiment, the positioner may allow the holder to move axially relative to the translation instrument.

An arm of a translation instrument may be pivotally coupled to an actuator of the translation instrument. The actuator may be a pair of lever arms or grips that are pivotally coupled together. When the grips are grasped and moved towards each other, the arm may move towards a holder placed within a positioner of the translation instrument. The arm may include a guide configured to mate with a guide of the holder. The arm may also include a rod engager. In an embodiment, the rod engager may be an indentation or groove in a body of the arm that contacts and holds a rod. The arm guide contacts the holder guide during use to adjust a position of the translation instrument relative to a fixation element. Grasping and moving the grips towards each other may rotate the arm so that the rod engager contacts a rod. Moving the grips closer together may bring the rod and the fixation element together. The holder guide may interact with the arm guide as the grips are moved towards each other. Contact of the holder guide with the arm guide may adjust a position of the translation instrument relative to the fixation element so that the rod and a rod opening of the fixation element may be brought together. After the rod is placed within the rod opening, the fixation element may be attached to the rod.

A guide of a fixation element holder and a guide of a translation instrument may interact to allow a rod held by the arm to be positioned in a rod opening of a fixation element. Using the holder guide and the translation instrument guide to adjust a position of the translation instrument relative to the fixation element may eliminate the need to manually guide a rod to a rod opening while simultaneously translating a vertebra or vertebrae to an adjusted position.

A translation instrument may include bias or spring members that influence a separation distance between grips of the instrument. The bias members may force the grips apart when a user does not apply a compressive force to the grips. When the grips are positioned fully apart from each other, the translation instrument is in an initial position. When the translation instrument is in the initial position, an arm of the translation instrument is in a position rotated away from a holder that is coupled to a positioner of the translation instrument. As the grips are moved together, the arm rotates towards the holder. If a user releases the grips, the biasing members may return the grips to the initial position.

A translation instrument may include a position retainer that resists forces applied to the grips by the bias members. In an embodiment, the position retainer may include a serrated member that is pivotally coupled to a first grip. The serrations may be configured to engage a portion of a second grip. The engaging portion of the second grip may be an end of the grip. The serrations are oriented to allow the grips to be moved towards each other, but resist movement of the grips away from each other. During use, a user may rotate the serrated member so that the member contacts the engaging portion of the second grip. The user may then move the first grip towards the second grip to rotate an arm towards a holder that is coupled to a positioner of the translation instrument. The user may stop the movement of the grips towards each other. If the user stops movement of the grips towards each other, the position retainer may allow the position of the arm to remain fixed relative to the holder. If the user desires to rotate the arm towards an initial position, the user may rotate the serrated member away from the engaging portion. Force applied to the grips may be removed to allow the bias members to return the grips, and the arm, towards the initial position.

In an embodiment, a position retainer of a translation instrument may be located at an end of the translation instrument. The location of the position retainer at the end of the translation instrument may allow a user convenient access to the position retainer during use with a hand that is not grasping the instrument. The location may also allow convenient access to the position retainer by a member of a surgical team who is not grasping the translation instrument.

A position retainer may also include a locking mechanism. The locking mechanism may be used to fix a position of a serrated member so that grips of the translation instrument are fixed relative to each other. Fixing the position of the grips relative to each other may inhibit accidental release of the position retainer. In an embodiment, the locking mechanism may be a hook that is pivotally attached to a second grip near an engaging portion of the second grip. When the hook is rotated so that the hook contacts the serrated member, movement of the grips towards or away from each other may be inhibited. When the hook is rotated away from the serrated member, the grips may be moved towards each other, or the serrated member may be rotated away from the engaging portion so that the grips may be moved away from each other.

An advantage of using a translation instrument to position a vertebra or vertebrae is that the translation instrument may simultaneously translate and vertically adjust the position of the vertebra or vertebrae. A position of a rod opening of a fixation element that may be coupled to an out-of-position vertebra may be adjusted relative to a position of a rod when the translation instrument is used. The translation instrument may ensure that the rod is placed within the rod opening during use. The fixation element may then be coupled to the rod. The translation instrument may eliminate the need to manually adjust a vertical position of the rod opening relative to the rod while simultaneously adjusting the lateral position of the rod opening relative to the rod.

A further advantage of a translation instrument may be that the translation instrument includes bias members that return the translation instrument to an initial position when grips of the instrument are released. The bias members may eliminate the need to manually close the grips and manually open the grips during use.

Another advantage of a translation instrument may be that the translation instrument includes a retention mechanism that inhibits grips of the translation instrument from returning to an initial position during use. The translation instrument may also advantageously include a locking member that fixes the position of the grips relative to each other and prevents accidental release or adjustment of the translation instrument.

Further advantages of a translation instrument may be that the translation instrument is sturdy, durable, lightweight, safe, simple, efficient, reliable and inexpensive; yet the translation instrument may also be easy to manufacture and use.

BRIEF DESCRIPTION OF THE DRAWINGS

Further advantages of the disclosed device and method will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Referring to the drawings, and more particularly to FIGS. 1–4, a translation instrument is indicated generally as 100. A translation instrument 100 may be used during a spinal fusion procedure to move a vertebra to a desired position relative to a spinal fixation system. A fixation element may be coupled to the vertebra. The fixation element may include a connector. A spinal fixation system may include a spinal rod that is coupled to two or more vertebrae. The translation instrument 100 may allow the connector to be snapped on the spinal rod so that the vertebra is moved to a desired position relative to the two or more vertebrae that are coupled to the spinal rod. The translation instrument 100 may simultaneously adjust a vertical position and lateral position of the connector relative to the spinal rod so that the spinal rod is snapped into an opening in the connector when the translation instrument is used.

Figure 5:
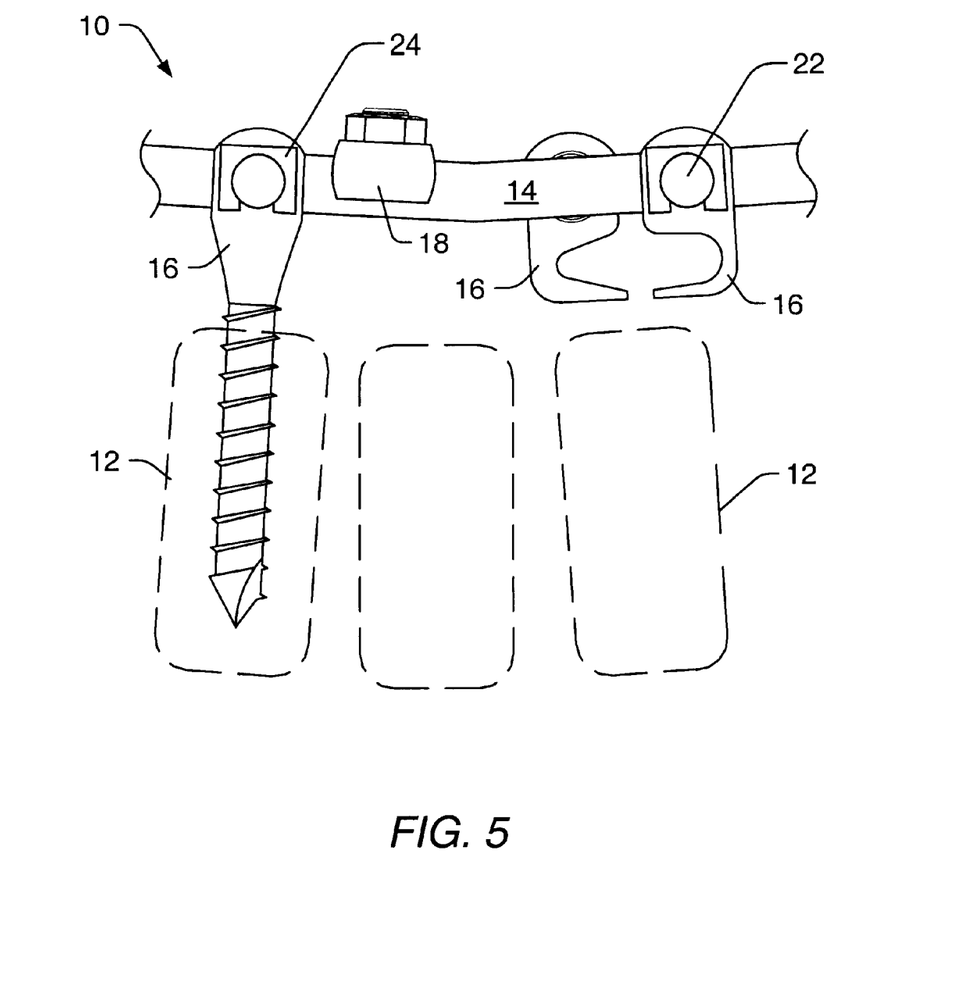
FIG. 5 depicts a schematic view of an embodiment of a spinal fixation system positioned adjacent to vertebrae.

FIG. 5 shows a portion of a spinal fixation system 10 placed in relation to representations of vertebral bodies 12. A spinal fixation system 10 may include rods 14, fixation elements 16, and transverse connectors 18. A pair of rods 14 (only one shown in FIG. 5) may be coupled on opposite sides of vertebral bodies 12 of a spine by fixation elements 16. Fixation elements 16 may include, but are not limited to, threaded fasteners and hooks. The fixation elements 16 may be, but are not limited to, bone screws and/or hooks. Transverse connectors 18 may be coupled across the spine to the pair of rods 14. A transverse connector may provide rigidity and stability to the spinal fixation system 10.

Figure 6:
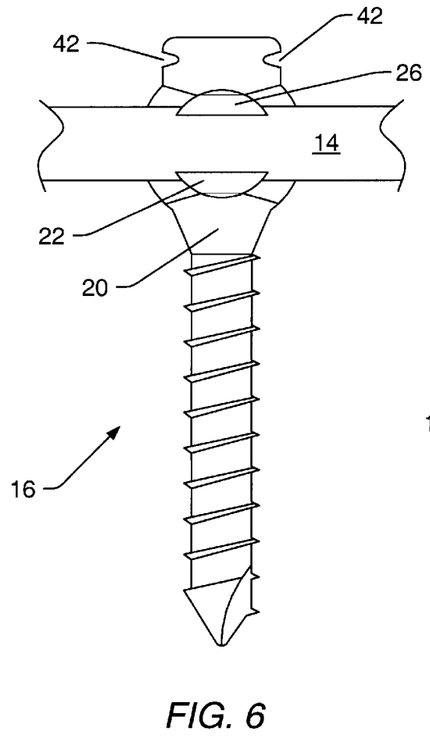
FIG. 6 depicts a front view of an embodiment of a fixation element coupled to a spinal rod.
Figure 7:
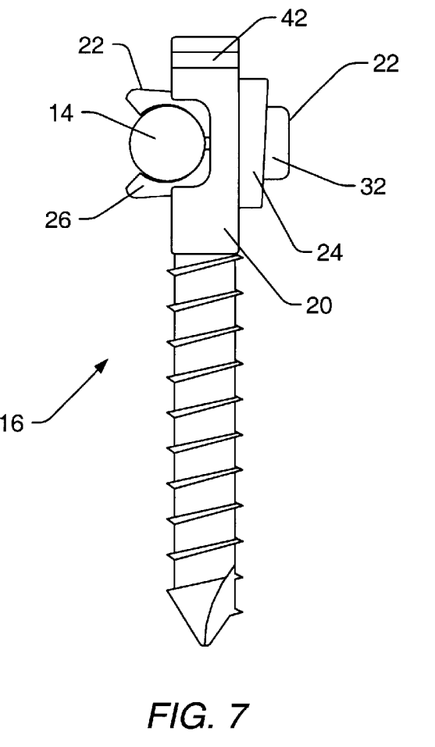
FIG. 7 depicts a side view of an embodiment of a fixation element coupled to a spinal rod.
Figure 8:
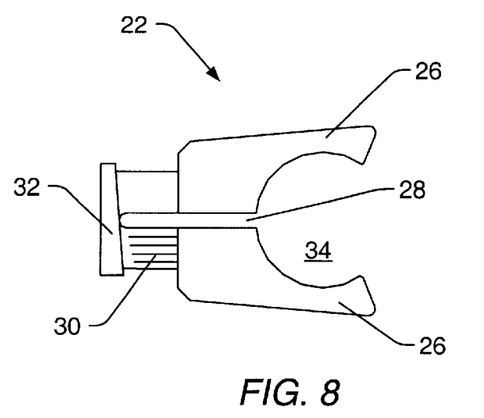
FIG. 8 depicts a side view of an embodiment of a fixation element connector.

During a spinal fixation procedure, a fixation element 16 may be attached to an out of position vertebra. The fixation element 16 may be, but is not limited to a bone screw or hook. FIG. 6 and FIG. 7 show front and side views, respectively, of an embodiment of a fixation element 16 attached to a spinal rod. The fixation element 16 may include body 20, connector 22 and clip 24. FIG. 8 depicts an embodiment of a connector. A connector 22 may include two arms 26, slot 28, textured surfaces 30 and end 32. A spinal rod 14 may be positioned in opening 34 between the two arms 26. The slot 28 between the arms may extend to end 32. The slot 28 may allow the arms 26 to deflect so that a spinal rod 14 may be snapped into the opening 34 between the two arms. When the connector 22 is positioned in the body 20, the connector arms 26 may be compressed towards each other by tapering inner surfaces of the body so that a spinal rod 14 positioned between the arms is secured to the connector and to the fixation element 16.

Figure 9:
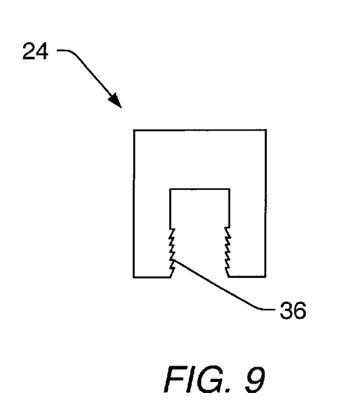
FIG. 9 depicts a front view of an embodiment of a fixation element clip.

FIG. 9 shows an embodiment of a clip 24. The clip 24 may be positioned between a body 20 of a fixation element and an end 32 of a connector 22 to secure a rod 14 to the connector, and the connector to the body. Textured surfaces 36 of the clip 24 may engage textured surfaces 30 of the connector 22 to form a secure connection. Texturing on the clip 24 and the connector 22 may be serrations, scoring, peening, or other roughening that enhances frictional or interlocking engagement between the clip and the connector. Texturing on the clip 24 may be a different type of texturing than texturing on the connector 22. In an embodiment, the connector may include threading and the clip may be a nut that mates to the threading of the connector, although a small working space in which the clip may be rotated may tend to weigh against the use of a threaded connection between the connector and the clip.

Figure 10:
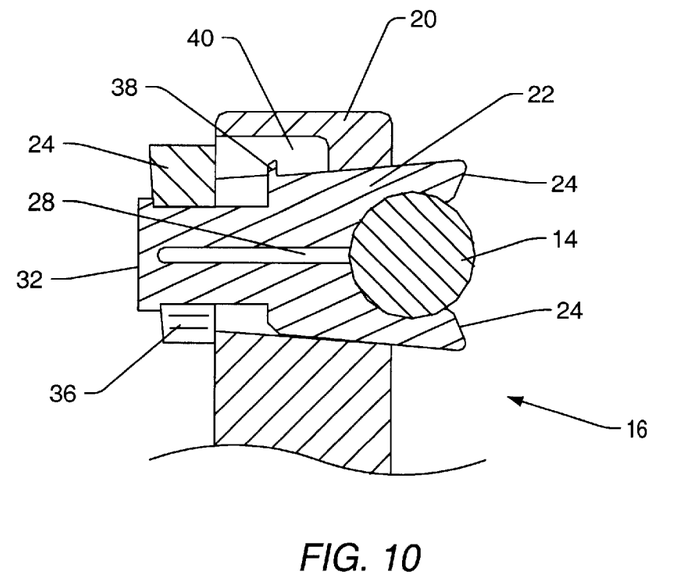
FIG. 10 depicts a cross-sectional view of a portion of an embodiment of a fixation element.
Figure 11:
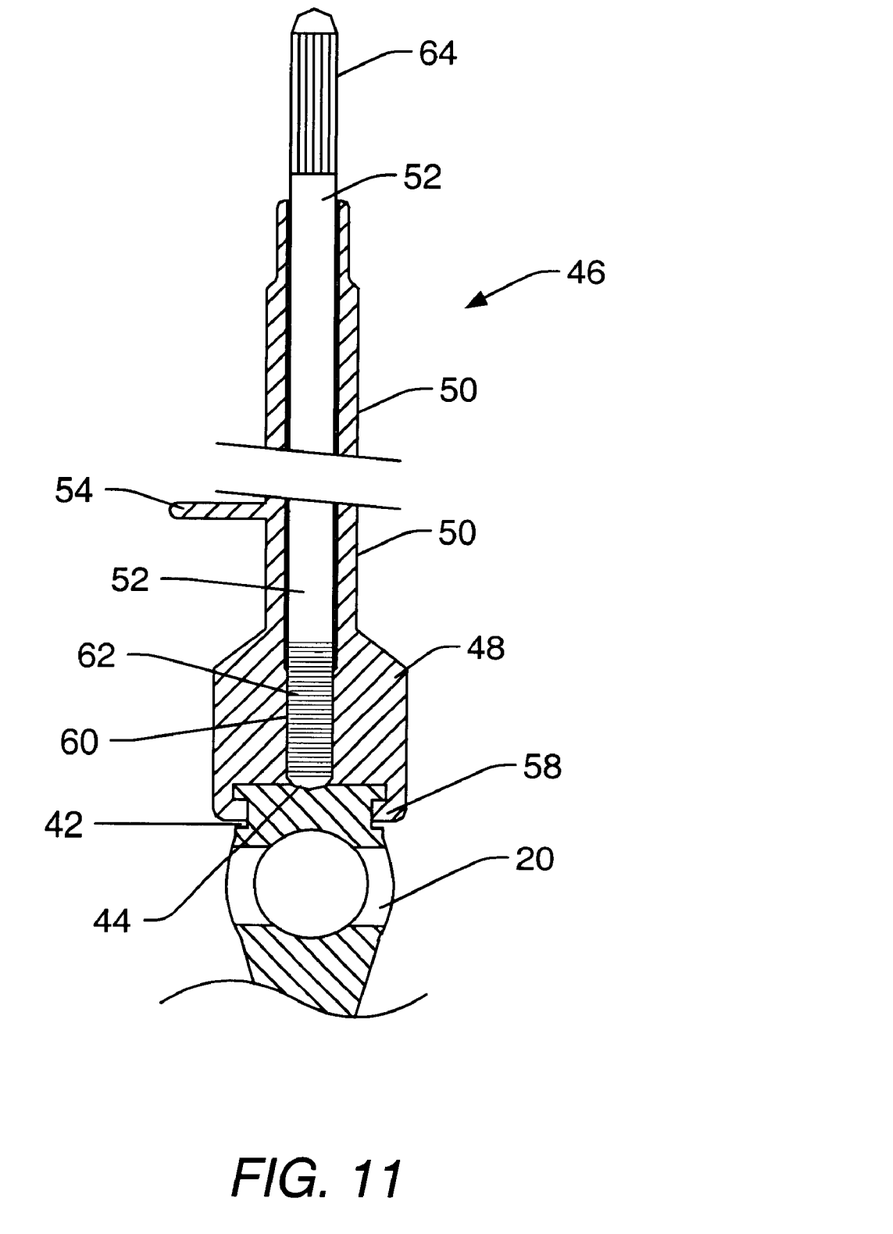
FIG. 11 depicts a partial cross sectional view of a holder that is coupled to a fixation element, wherein a shaft of the holder is not shown in cross section.

FIG. 10 shows an embodiment of a portion of a fixation element 16. A connector 22 of the fixation element 16 may include raised portion 38 that allows the connector to be attached to a body 20 of the fixation element such that removal of the connector from the body is inhibited. Attaching the body 20 and the connector 22 together may allow for insertion of the connector and fixation element 16 into a patient as a single unit instead of in two separate pieces. To attach the connector 22 to the body 20, arms 26 of the connector may be compressed and the connector may be inserted into the of the fixation element 16. Expansion of the arms 26 back to an initial position may inhibit removal of the connector 22 from the body in an opposite direction to the direction of insertion. The raised portion 38 may be placed in recess 40 of the body 20. The raised portion 38 may contact the body 20 to inhibit the connector 22 from being removed from the body in the direction of insertion of the connector into the body. The recess 40 may have a width that limits rotation of the connector 22 to a range that the fixation element 16 may be skewed to relative to a rod 14. In embodiments of fixation elements, the range of rotation of the connector 22 in the body 20 is limited to about ±350, to about ±25°, or to about ±15°. In other fixation element embodiments, the range of rotation of the connector in the body is limited to less than +15°, FIG. 11 shows a cross sectional view of a holder coupled to a body of a fixation element. A body 20 of a fixation element 16 may include grooves 42 and indention 44. The grooves 42 and indention 44 may allow the fixation element to be coupled to holder 46.

A holder 46 may include head 48, hollow shaft 50, shaft 52 and guide 54. The head 48 may include wall 56 (shown in FIG. 1) that limits an insertion depth of a fixation element body 20 into the holder 46. The wall 56 may also apply force to the fixation element 16 during a spinal fusion procedure. The force applied by the wall 56 may allow a rod of a spinal fixation system to be placed in a connector of the fixation element to properly align a vertebra to which the fixation element is attached with respect to the rod and the vertebrae to which the rod is attached. The head 48 may include end tips 58 that fit within grooves 42 of the fixation element 16. The head 48 may include an internal threading 60 that engages threading 62 of the shaft 52. The shaft 52 may be positioned in the hollow shaft 50. Rotating in a clockwise direction end 64 of the shaft 52 may advance the shaft relative into the head 48. Second end 64 of the shaft 52 may include knurling or other type of texturing that allows a user to easily grip and rotate the shaft 52. Guide 54 may be an arm extending from a side of the hollow shaft 50. The hollow shaft may be placed in positioners of a translation instrument 100.

Grooves 42 of a fixation element 16 may slide on end tips 58 of a holder 46 until the fixation element contacts an internal surface of holder wall 56. A shaft 52 of the holder 46 may be rotated in a first direction, typically in a clockwise direction, to advance the shaft relative into a head 48 of the holder. End 62 of the shaft 52 may contact a surface of the indentation 44 in the fixation element 16. Contact of the shaft 52 with the fixation element 16 may provide a force against the fixation element that securely attaches the fixation element to the holder 46. Rotating the shaft 52 in an opposite direction, typically counter-clockwise, allows the holder 46 to be removed from the fixation element 16.

FIGS. 1–4 show embodiments of translation instruments 100. A translation instrument 100 may include positioners 102, arm 104, and grips 106. The translation instrument 100 may be used to place a spinal rod that is coupled to two or more vertebrae in a connector of a fixation element that is coupled to an out of position vertebra. A fixation element holder 46 may be placed within positioners 102 of the translation instrument 100. Positioners 102, arm 104, and grips 106 of the translation instrument 100 may be pivotally coupled together. Pivotal connections 108 joining the grips 106 to the arm 104 may allow the arm to rotate when the grips are moved towards each other. The pivotal connections 108 allow the grips 106 to move towards or away from each other. The arm 104 of the translation instrument 100 may rotate towards a fixation element holder 46 that is placed within the positioners 102 when the grips 106 are moved towards each other.

Figure 4:
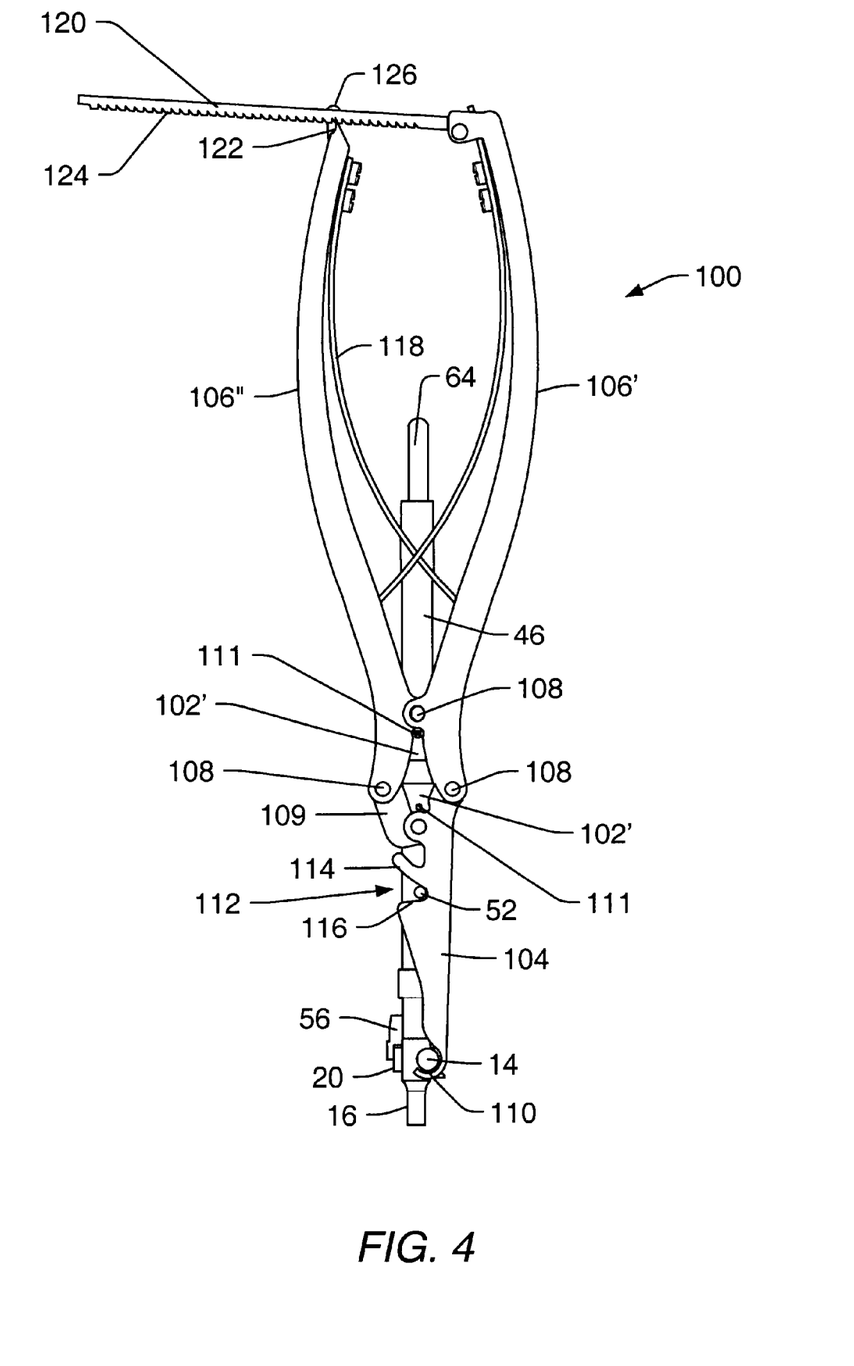
FIG. 4 depicts a back view of an embodiment of a translation instrument that is coupled to a holder and fixation element when the translation instrument is in a closed position.

A first positioner 102' may be pivotally coupled to grips 106 of a translation instrument 100 (shown in in FIG. 4). A second positioner 102" may be pivotally coupled to linking arm 109 and to arm 104. The positioners may include pins 111 that limit a range of rotational motion of the positioners relative to the grips 106. Limiting a rotational range of motion of the positioners 102 may facilitate placement of a holder 46 in the positioners.

Positioners 102 of a translation instrument 100 may retain a fixation element holder 46. The positioners 102 may allow axial movement of holder shaft 52 relative to the translation instrument 100. The positioners 102 may inhibit lateral and rotational motion of the holder 46 relative to the translation instrument 100.

Arm 104 of a translation instrument 100 may include rod engager 110 and guide 112. The rod engager 110 may contact a rod 14 during use. The rod engager 110 may be an indentation or groove in the arm 104 that contacts the rod 14 and secures the rod to the translation instrument 100 during use.

A guide 112 of a translation instrument arm 104 may contact a holder guide 54. The translation instrument guide 112 may be a channel between a first surface 114 and a second surface 116. Contact of the first surface 114 and/or the second surface 116 against a guide 54 of a fixation element holder 46 may adjust the position of holder 46 relative to the translation instrument 100. First surface 114 may contact the holder guide 54 when hollow shaft 50 is placed in positioners 102 and the translation instrument is moved towards the holder guide 54. Position adjustment of the fixation element holder 46 relative to the translation instrument 100 allows a rod 14, which is engaged by the translation instrument arm 104, to be positioned within rod opening 34 of a fixation element connector 22 when grips 106 of the translation instrument are squeezed together.

Figure 1:
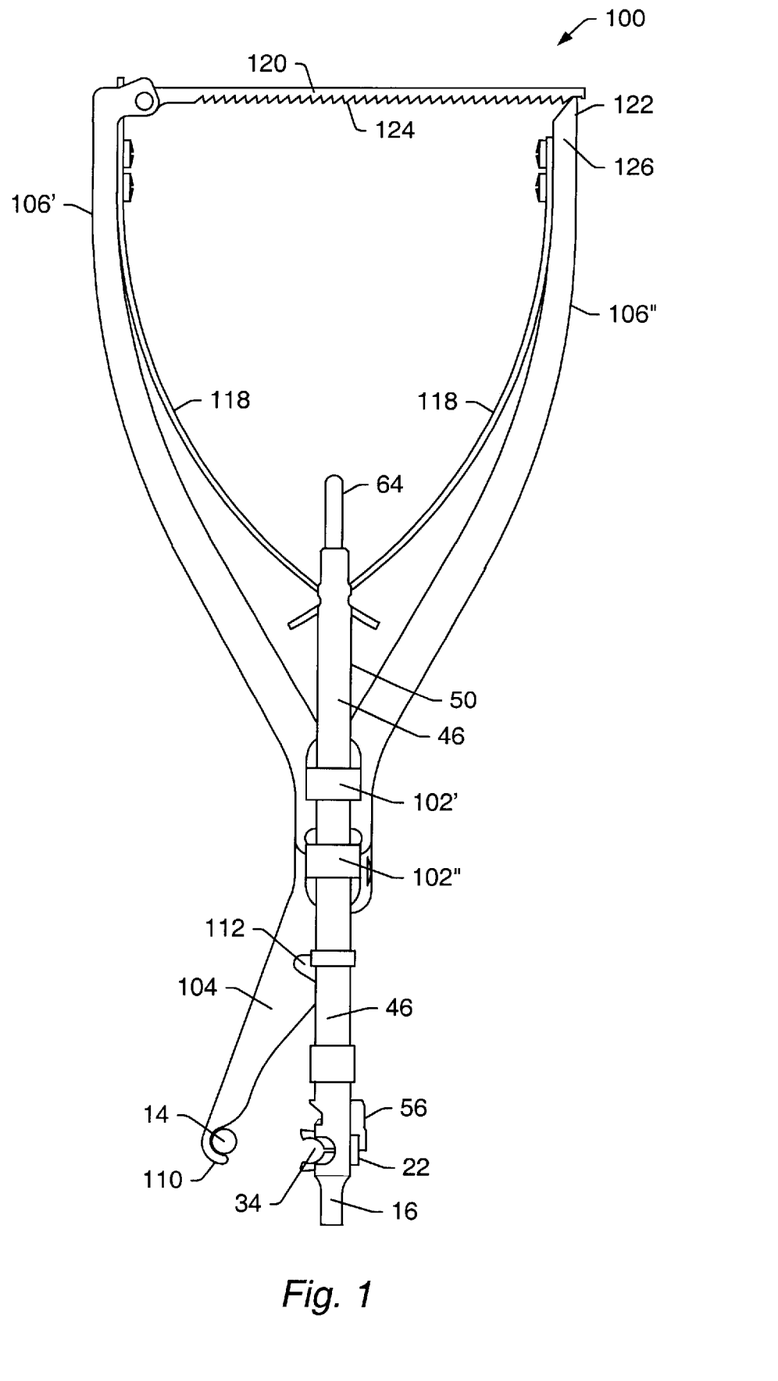
FIG. 1 depicts a front view of an embodiment of a translation instrument that is coupled to a holder and fixation element when the translation instrument is in an initial position.
Figure 2:
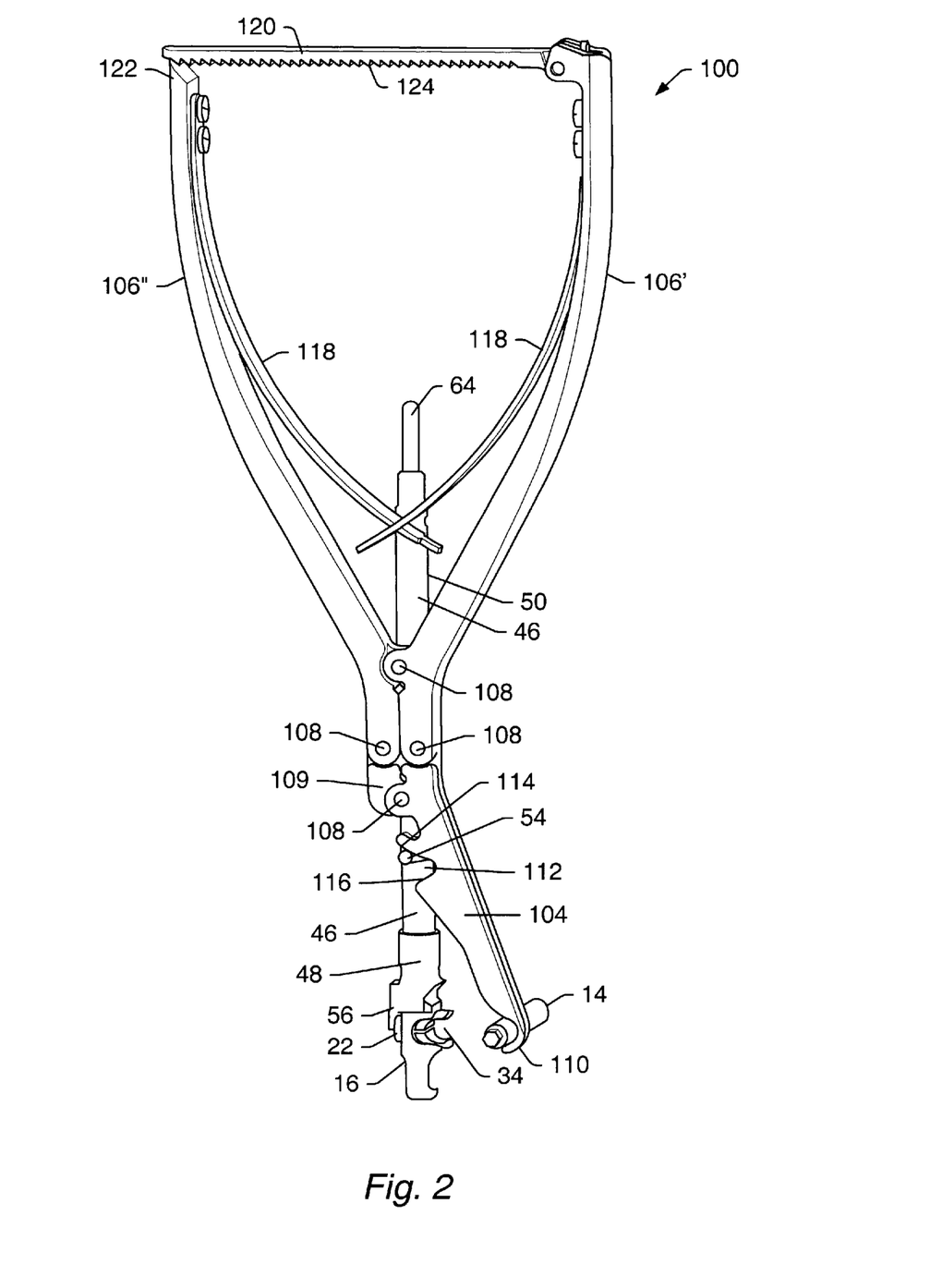
FIG. 2 depicts a back view of an embodiment of a translation instrument that is coupled to a holder and fixation element when the translation instrument is in an initial position.
Figure 3:
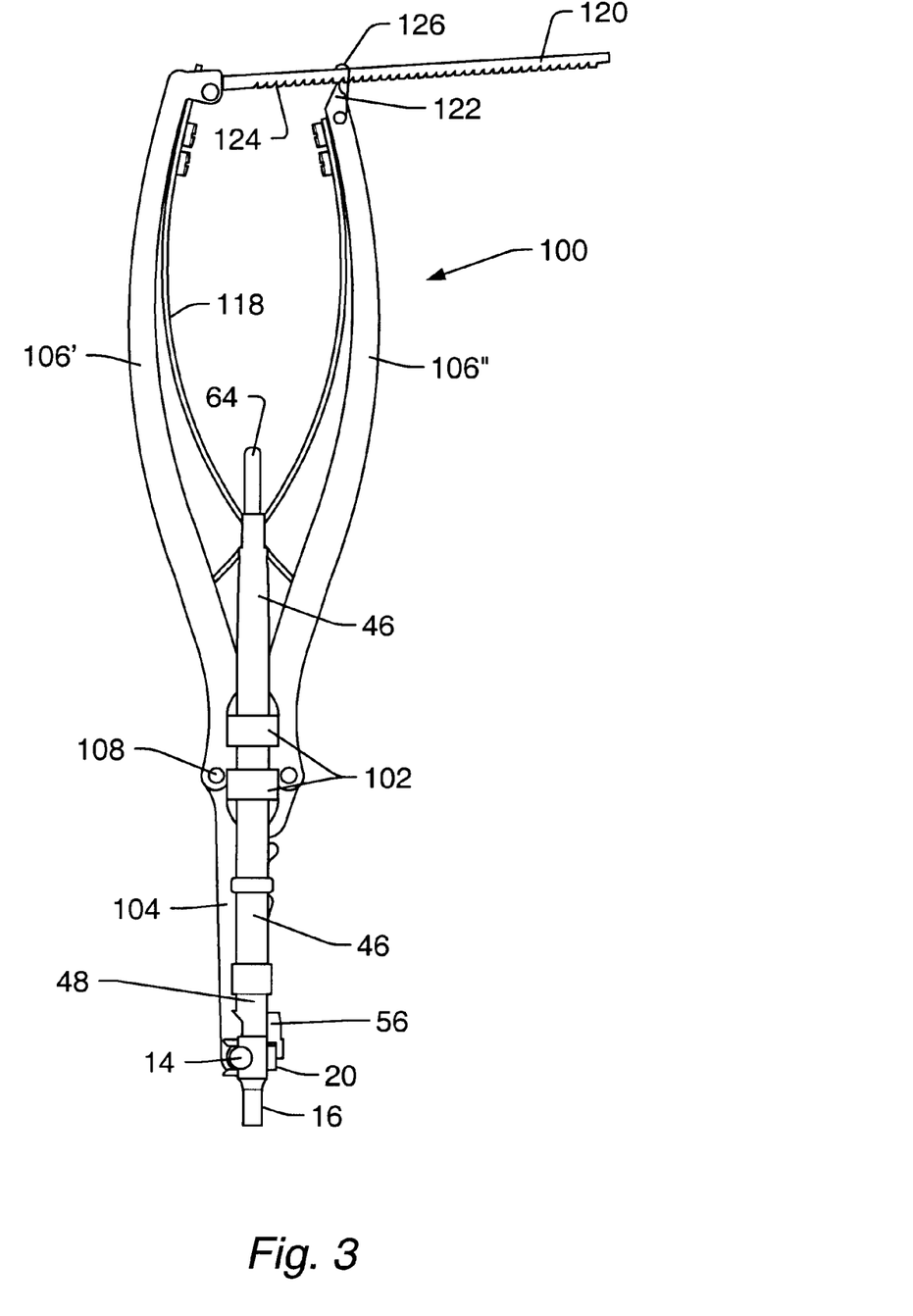
FIG. 3 depicts a front view of an embodiment of a translation instrument that is coupled to a holder and fixation element when the translation instrument is in a closed position.

Spring members 118 may be coupled to grips 106 of a translation instrument 100. The spring members 118 may apply forces to the grips 106 that tend to separate the grips. When the grips 106 are fully separated, the translation instrument 100 is in an initial position. FIG. 1 and FIG. 2 show translation instruments 100 in initial positions. When the translation instrument 100 is in the initial position, the arm 104 may be rotated away from a fixation element holder 46 that is placed within positioners 102 of the translation instrument. In an embodiment, the first guide surface 114 may contact fixation element holder guide 54 if a translation instrument in an initial position is moved towards a fixation element 16 attached to the holder 46. Contact of the first surface 114 of the guide 112 against the fixation element holder guide 54 may limit insertion depth of the translation instrument 100 relative to the fixation element 16. The grips 106 may be squeezed together to place the translation instrument in a closed position. FIG. 3 and FIG. 4 show translation instruments 100 in closed positions.

Retainer 120 may be rotationally coupled to a first grip 106' of the translation instrument. The retainer 120 may be rotated towards or away from a second grip 106". The retainer 120 may contact retainer stop 122. The retainer stop 122 may interact with the retainer 120 to inhibit separation of the grips 106 from each other if a user releases the grips. The retainer 120 may be rotationally coupled near an end of first grip 106', and retainer stop 122 may be an end of second grip 106" of the translation instrument 100. A retainer 120 and a retainer stop 122 may be positioned at other locations along lengths of the grips 106. A retainer 120 may include serrations 124. The retainer stop 122 may engage the serrations 124. Interaction of the serrations 124 with the retainer stop 122 may allow the grips 106 to move towards each other if a user grasps the grips and forces the grips towards each other. Interaction of the serrations 124 with the retainer stop 122 may inhibit the grips 106 from separating if a user releases the grips. The interaction of the retainer stop 122 and the serrations 124 may inhibit spring members 118 from returning a translation instrument 100 to an initial position.

Lock 126 may be used to inhibit undesired rotation of the retainer 120 away from a second grip 106". The lock 126 may be a hook that is pivotally coupled to the second grip 106". When the lock 126 is rotated to engage the retainer 120, as shown in FIG. 4, the lock may inhibit movement of the grips 106 towards or away from each other. The lock 126 may be used to inhibit unintentional release of the retainer 120 during a surgical procedure.

A translation instrument 100 may be used to move an out-of-position vertebra or vertebrae 12 and a rod 14 of a spinal stabilization system 10 together. Fixation elements 16 may be used to couple rods 14 to vertebrae to form the stabilization system 10. Transverse connectors 18 may be coupled to the rods 14 to provide rigidity and stability to the stabilization system 10. A fixation element 16 may be coupled to an out-of-position vertebrae. In an embodiment, the fixation element 16 may be a bone screw that is threaded into the out-of-position vertebra.

A fixation element holder 46 may be coupled to the fixation element 16. The fixation element 16 may have a connector 22 positioned within a body 20 of the fixation element. Grooves 42 of the fixation element 16 may slide along end tips 58 of the holder 46 until the fixation element contacts inner surface of wall 56 of the holder. Holder shaft 52 may be rotated to couple the holder 46 and the fixation element body 20 together. The fixation element holder 46 may be placed within positioners 102 of the translation instrument 100. The translation instrument 100 may be moved towards the fixation element 16 until a first surface 114 of the guide 112 contacts holder guide 54. A rod 14 of a spinal stabilization system 10 that is coupled to two or more vertebrae may be positioned in rod engager 110. Grips 106 of the translation instrument 100 may be grasped and moved towards each other so that the arm 104 moves towards the rod to the connector. As the grips 106 are forced together, the guide 112 of the translation instrument 100 and the holder guide 54 adjust the position of the rod 14 relative to the connector so that the rod 14 and the rod opening 34 of the fixation element 16 are brought together such that the rod snaps into the connector. The translation instrument 100 may be removed from the holder 46 and the holder may be removed from the fixation element 16. A clip 24 may be placed between a connector end 32 and the fixation body 20 to secure the fixation element 16, connector 22 and rod 14 together.

During a translation maneuver, movement of an out-of-position vertebra 12 relative to a spinal rod may be achieved and the application of increasing force to the grips 106 of the translation instrument 100. A retainer 120 may be used during a translation maneuver to inhibit unintentional movement of an arm 104 of the translation instrument 100 away from a fixation element holder 46. The retainer 120 may be rotated to a position where serrations 124 of the retainer engage a retainer stop 122. If the position of the grips 106 relative to each other will not be changed for a period of time, a lock 126 of the translation instrument 100 may rotated so that the lock 126 engages the retainer 120 and holds the grips of the translation instrument at a fixed separation distance. Use of the lock 126 may inhibit the grips 106 from being moved towards or away from each other. When the position of the arm 104 of the translation instrument 100 needs to be adjusted again, the lock 126 may be disengaged from the retainer 120 and the grips 106 may be moved towards each other. If it is desired to move the arm 104 away from the fixation instrument holder 46 during a translation maneuver, a user may rotate the retainer 120 away from the retainer stop 122 and apply less force to the grips so that the separation between the grips 106 increases. Increasing the separation distance between the grips 106 allows the arm 104 to move away from the fixation element holder 46.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An instrument for reducing a rod to a fixation element, comprising:
   an arm configured to engage the rod, the arm having a guide and a rod engager;
   positioners configured to slidably couple the instrument to the fixation element; and
   wherein the guide is configured to engage a protrusion extending from the fixation element so that the arm moves the rod into an opening in the fixation element when the protrusion extending from the fixation element traces at least a portion of a pathway defined by the guide.

2. The instrument of claim 1, wherein the arm moves along an arced path.

3. The instrument of claim 1, wherein the guide comprises a channel in the arm.

4. The instrument of claim 1, wherein the positioners are configured to prevent the holder from rotating in the positioners and to allow the holder to slide through the positioners during use.

5. The instrument of claim 1, wherein the rod engager comprises an arcuate portion that has a radius of curvature that substantially matches a radius of the rod.

6. The instrument of claim 1, wherein the instrument further comprises two grips, and wherein movement of the grips relative to each other moves the arm.

7. The instrument of claim 6, wherein the two grips are pivotally connected to the arm.

8. The instrument of claim 1, wherein the instrument further comprises a spring member that biases the arm to an initial position.

9. The instrument of claim 1, wherein the instrument further comprises a retainer configured to inhibit return of the arm to an initial position.

10. A bone translation system, comprising:
    a holder configured to couple to a fixation element during use, wherein the holder comprises a protrusion and wherein the fixation element is configured to couple to a first bone;
    a connector coupled to the fixation element;
    an instrument configured to move a rod coupled to a second bone into the connector, the instrument comprising:
    positioners configured to couple the holder to the instrument;
    an arm configured to engage the spinal rod during use; and
    a guide on the arm, the guide configured to engage the protrusion of the holder.

11. The system of claim 10, wherein the arm comprises a rod engager configured to couple to the rod.

12. The system of claim 10, wherein the arm travels an arced path during translation.

13. The system of claim 10, wherein the protrusion on the holder is configured to advance along the guide during use.

14. The system of claim 10, wherein the positioners are configured to allow the holder to axially move.

15. The system of claim 10, wherein the fixation element is a bone screw.

16. The system of claim 10, wherein the fixation element is a hook.

17. An instrument for reducing a spinal rod to a spinal fixation element, comprising:

positioners to engage a fixation element holder, wherein the positioners are configured to prevent the holder from rotating freely within the positioners during use;

an arm configured to engage the spinal rod during use, the arm comprising a guide;

two grips;

biasing members configured to force the grips to an initial position; and a retainer configured to maintain a partially reduced offset between the spinal rod and the spinal rod connector;

wherein moving the two grips towards each other moves the arm toward the holder, and wherein the guide on the arm has a length configured to contact a protrusion on the holder to align the spinal rod to a connector coupled to the spinal fixation element during use.

18. The instrument of claim 17, wherein the arm comprises a void or hook to engage the spinal rod during use.

19. The instrument of claim 17, wherein the instrument is configured to reduce the spinal rod to the spinal rod connector in an arcuate direction during use.

20. The instrument of claim 17, wherein the guide comprises a surface configured to engage the protrusion on the holder to abut the spinal rod with the connector during use.

21. The instrument of claim 17, wherein the positioners are configured to allow the holder to slidably advance through the positioners during use.

22. The instrument of claim 17, wherein the spinal fixation element is configured to attach to a vertebra by a hook, a clamp, or a threaded region.

23. The instrument of claim 17, wherein the two grips are pivotally connected.

24. The instrument of claim 17, wherein the two grips are pivotally connected to the arm.

25. A rod translation system for moving a first bone closer to a second bone, comprising:

a fixation element configured to couple to the first bone, the fixation element comprising a connector;

a holder configured to couple to the fixation element, the holder comprising a holder guide;

a rod configured to be coupled to the second bone;

an instrument configured to slidably couple to the holder, the instrument comprising a movable arm, wherein the movable arm comprises an instrument guide and a rod engager; and wherein the holder guide is configured to engage the instrument guide to position the rod into the connector when the instrument is activated.

26. The system of claim 25, wherein the holder guide comprises an extension, and wherein the instrument guide comprises a channel.

27. The system of claim 25, wherein the connector is configured to couple to the fixation element such that removal of the connector from the fixation element is inhibited.

28. The system of claim 25, wherein the connector comprises a pair of arms and a raised surface, wherein the raised surface is positionable within a recess of the fixation element.

29. The system of claim 25, wherein the fixation element comprises a hook.

30. The system of claim 25, wherein the fixation element comprises a bone screw.

31. The system of claim 25, wherein the instrument comprises positioners configured to couple the holder to the instrument, and wherein the positioners allow axial movement of the holder.

32. The system of claim 25, wherein the rod engager comprises a groove in the arm.

33. The system of claim 25, wherein the instrument comprises grips, and wherein the grips control movement of the arm.

34. The system of claim 25, wherein the instrument comprises a pair of grips and a retainer, and wherein the retainer is configured to inhibit movement of the grips relative to each other in a first direction when the retainer is in a first position.

35. The system of claim 34, further comprising a lock for the retainer.

36. The system of claim 25, wherein the instrument further comprises a spring member that applies force to the instrument to separate grips of the instrument.

37. The system of claim 25, further comprising a clip positionable between an end of the connector and a body of the fixation element.

38. The system of claim 37, wherein the clip comprises at least one textured surface configured to engage a surface of the connector to inhibit removal of the clip from the connector.

39. The system of claim 37, wherein the connector comprises at least one textured surface configured to engage a surface of the clip to inhibit removal of the clip from the connector.

40. A method of reducing a spinal rod to a spinal fixation element, comprising:

attaching a holder to the spinal fixation element;

coupling the holder to an instrument;

engaging the spinal rod with an arm of the instrument;

aligning the spinal rod to a spinal rod connector coupled to the fixation element by contacting a guide on the arm with a protrusion on the holder; and reducing an offset between the spinal rod and the spinal rod connector.

41. The method of claim 40, further comprising attaching the fixation element to a vertebra prior to attaching a holder to the fixation element.

42. The method of claim 40, wherein the method is repeated on two sides of a spine.

43. The method of claim 40, wherein coupling the holder to the instrument comprises inserting the holder in positioners extending from the instrument.

44. The method of claim 40, wherein engaging the spinal rod with the arm of the instrument comprises engaging the spinal rod with a void or hook in the arm.

45. The method of claim 40, wherein reducing the offset between the spinal rod and the spinal fixation element comprises moving the spinal rod in an arcuate direction.

46. The method of claim 40, wherein reducing the offset between the spinal rod and the spinal fixation element comprises moving the fixation element in an arcuate direction.

47. The method of claim 40, wherein reducing the offset between the spinal rod and the spinal fixation element comprises advancing the protrusion of the holder along the guide on the arm.

48. The method of claim 40, wherein reducing the offset between the spinal rod and the spinal fixation element comprises moving a first grip and a second grip.

49. The method of claim 48, wherein moving the first grip and the second grip comprises moving the first grip toward the second grip, wherein the first and second grips are pivotally connected.

50. The method of claim 48, wherein moving the first grip and the second grip comprises overcoming tension applied to the first grip and the second grip by biasing members.

51. The method of claim 48, wherein moving the first grip and the second grip comprises partially moving the first grip and the second grip and securing the grips in a partially closed position by a retainer.

52. A method of reducing a rod to a fixation element, comprising:
- attaching a holder to the fixation element; and
- slidably coupling the holder to an instrument;
- coupling a rod engager to a rod;
- activating the instrument to place the rod in a connector of the fixation element, wherein a portion of the holder engages a portion of the instrument to guide the rod into the connector.

* * * * *